US011574702B2

(12) United States Patent
Jafri et al.

(10) Patent No.: US 11,574,702 B2
(45) Date of Patent: Feb. 7, 2023

(54) MINING ALL ATOM SIMULATIONS FOR DIAGNOSING AND TREATING DISEASE

(71) Applicant: George Mason University, Fairfax, VA (US)

(72) Inventors: Mohsin Saleet Jafri, Potomac, MD (US); Matthew McCoy, Washington, DC (US)

(73) Assignee: George Mason University, Fairfax, VA (US)

( * ) Notice: Subject to any disclaimer, the term of this patent is extended or adjusted under 35 U.S.C. 154(b) by 984 days.

(21) Appl. No.: 16/225,789

(22) Filed: Dec. 19, 2018

(65) Prior Publication Data
US 2019/0189243 A1 Jun. 20, 2019

Related U.S. Application Data

(60) Provisional application No. 62/608,168, filed on Dec. 20, 2017.

(51) Int. Cl.
*G16B 20/20* (2019.01)
*C12Q 1/6827* (2018.01)
*C12Q 1/6883* (2018.01)
*G16B 10/00* (2019.01)
*G16B 35/00* (2019.01)
*G16B 40/20* (2019.01)
*G16B 50/50* (2019.01)
*G16B 50/10* (2019.01)
*G16B 5/20* (2019.01)
*G16B 40/30* (2019.01)
*G16B 20/00* (2019.01)

(52) U.S. Cl.
CPC ............ *G16B 20/20* (2019.02); *C12Q 1/6827* (2013.01); *C12Q 1/6883* (2013.01); *G16B 5/20* (2019.02); *G16B 10/00* (2019.02); *G16B 20/00* (2019.02); *G16B 35/00* (2019.02); *G16B 40/20* (2019.02); *G16B 40/30* (2019.02); *G16B 50/10* (2019.02); *G16B 50/50* (2019.02)

(58) Field of Classification Search
None
See application file for complete search history.

(56) References Cited

PUBLICATIONS

Wang et al. Personalized prediction of EGFR mutation-induced drug resistance in lung cancer Scientific Reports vol. 3, article 2855 (Year: 2013).*
Saladino et al. Modeling the effect of pathogenic mutations on the conformational landscape of protein kinases Current Opinion in Structural Biology vol. 37, pp. 108-114 (Year: 2016).*
Bhakat et al. An integrated molecular dynamics, principal component analysis and residue interaction network approach reveals the impact of M184V mutation on HIV reverse transcriptase resistance to lamivudine Molecular Biosystems vol. 10, article 2215 (Year: 2014).*
Hou et al. Predicting drug resistance of the HIV-1 protease using molecular interaction energy components Proteins vol. 74 pp. 837-846 (Year: 2009).*
Morozov et al. Protein-DNA binding specificity predictions with structural models Nucleic Acids Research vol. 33, pp. 5781-5798 (Year: 2005).*
Shao et al. Clustering Molecular Dynamics Trajectories: 1. Characterizing the Performance of Different Clustering Algorithms Journal of Chemical Theory and Computation vol. 3 pp. 2312-2334 (Year: 2007).*

* cited by examiner

*Primary Examiner* — John S Brusca
(74) *Attorney, Agent, or Firm* — Morris, Manning & Martin, LLP; Daniel E. Sineway, Esq.

(57) ABSTRACT

The present disclosure describes methods for determining the functional consequences of mutations. The methods include the use of machine learning to identify and quantify features of all atom molecular dynamics simulations to obtain the disruptive severity of genetic variants on molecular function.

20 Claims, 10 Drawing Sheets
(6 of 10 Drawing Sheet(s) Filed in Color)

| CaM Variant | Cluster ID | % of variant Population | | CaM Variant | Cluster ID | % of variant Population |
|---|---|---|---|---|---|---|
| D130G | 2 | 19.9 | | N54I | 12 | 12.47 |
| | 3 | 15.83 | | | 18 | 10.93 |
| | 4 | 24.87 | | | 24 | 32.23 |
| | 9 | 10.1 | | | 37 | 18.2 |
| D96V | 15 | 15.07 | | N98S | 16 | 12.2 |
| | 16 | 14.57 | | | 27 | 11.4 |
| | 4 | 12.43 | | | 33 | 16.47 |
| | 5 | 28.67 | | | 39 | 13.57 |
| F142L | 18 | 12.97 | | wildtype | 4 | 36.7 |
| | 3 | 20.7 | | | 6 | 10.07 |
| | 4 | 17.57 | | | 7 | 11.23 |
| | 6 | 13.3 | | | | |

Fig. 2D

MINING ALL ATOM SIMULATIONS FOR DIAGNOSING AND TREATING DISEASE

CROSS REFERENCE TO RELATED APPLICATIONS

This application claims the benefit of U.S. Provisional Patent Application No. 62/608,168, filed on Dec. 20, 2017, which is hereby incorporated by reference in its entirety.

GOVERNMENT SUPPORT

This invention was made with government support under grant number R01 HL105239 and number U01 HL116321 awarded by the National Institutes of Health. The government has certain rights in the invention.

TECHNICAL FIELD

The present disclosure discloses the use of molecular dynamics simulation and machine learning for diagnosing and treating disease.

BACKGROUND

Molecular dynamics (MD) simulation is a computer method for studying the movements of atoms and molecules. MD provides the time dependent behavior of atoms and molecules in a system. MD simulation was developed in the late 70s. With the development of high performance computing, MD simulation has advanced from simulating several hundred of atoms to simulating 500,000 atoms or more.

MD is the method of choice for studying large molecules such as proteins and nucleic acids. Proteins were once thought to have a rigid structure. It is now believed that proteins are highly dynamic structures. The study of the dynamics of macromolecules, such as protein and nucleic acid, is complex and requires computers and the in silico study of the macromolecular structure and macromolecular dynamics in order to obtain accurate information.

Machine learning (ML) evolved from the study of pattern recognition and computational learning theory in artificial intelligence. ML provides systems with the ability to automatically learn and improve from experience without being explicitly programmed. Thus, ML focuses on the development of computer programs that can access data and use it to learn for themselves. In recent years, researchers have shown that MD simulations and ML can be integrated to create more accurate in silico computer prediction models. As an example, these models can be used to quickly predict new compounds that have potential as drug candidates.

The Human Genome Project has enabled the ability to sequence the human genome as well as genomes for other species, which has in turn permitted the identification of sequence variations in the human gene genome. These sequence variations are caused by mutations which result in diseases, different reactions to drugs, and natural phenotypic variations in individuals in the population. It is essential understand how these mutations alter protein function.

Recent studies using MD and ML have only provided limited insight into the role of these mutations in the human and other species. There is a need to develop an accurate method of using MD and ML, for example, for predicting variants associated with a particular disease in order to provide proper and optimal treatment or with a particular trait that might be desirable for a crop or animal.

SUMMARY

The present disclosure describes novel computational methods that enable the characterization of the functional consequences of mutations in the genome. The methods include the use of ML to identify and quantify features of all atom MD simulations to obtain the effect and disruptive severity of genetic variants on molecular function. The basic steps of the methods integrate the technologies of MD and ML and are as follows: (1) use molecular dynamics simulations to create an ensemble of structures for a macromolecule; (2) perform similar calculations of a collection of mutations on the macromolecule; (3) obtain quantitative measures on information about the structure and function of the macromolecule, for example, size, shape, binding affinity, torsion, and bending; (4) compare the information obtained from the collection mutations with that of the wildtype or naturally occurring macromolecule to determine the deviation of each mutation from the wildtype macromolecule; and (5) use principle component analysis on this quantitative information set to find the main measures governing the mutations. By considering the principal component that characterize the separation of wildtype and variant structures, the amount of deviation between mutants (variants) can be measured compared to wildtype.

This calculated amount of deviation characterizing the mutant correlates with the amount of deviation from normal function (the function of the wildtype macromolecule) to provide information on the severity of a disease that mutation can cause.

In embodiments, the macromolecule is a protein or a nucleic acid of interest, and the mutation causes a disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2D show structural clustering of individual variant trajectories. The ribbon backbone for a representative structure from each distinct sub-populations of variant structures observed during the simulated trajectories show a wide range of local structural dynamics in the (A) N-lobe, (B) C-lobe, and (C) linker regions of calmodulin. D. The clustering of RMSD between representative structures of variant sub-populations show no clear separation between variants and wildtype structures.

DETAILED DESCRIPTION

Figure 1A:
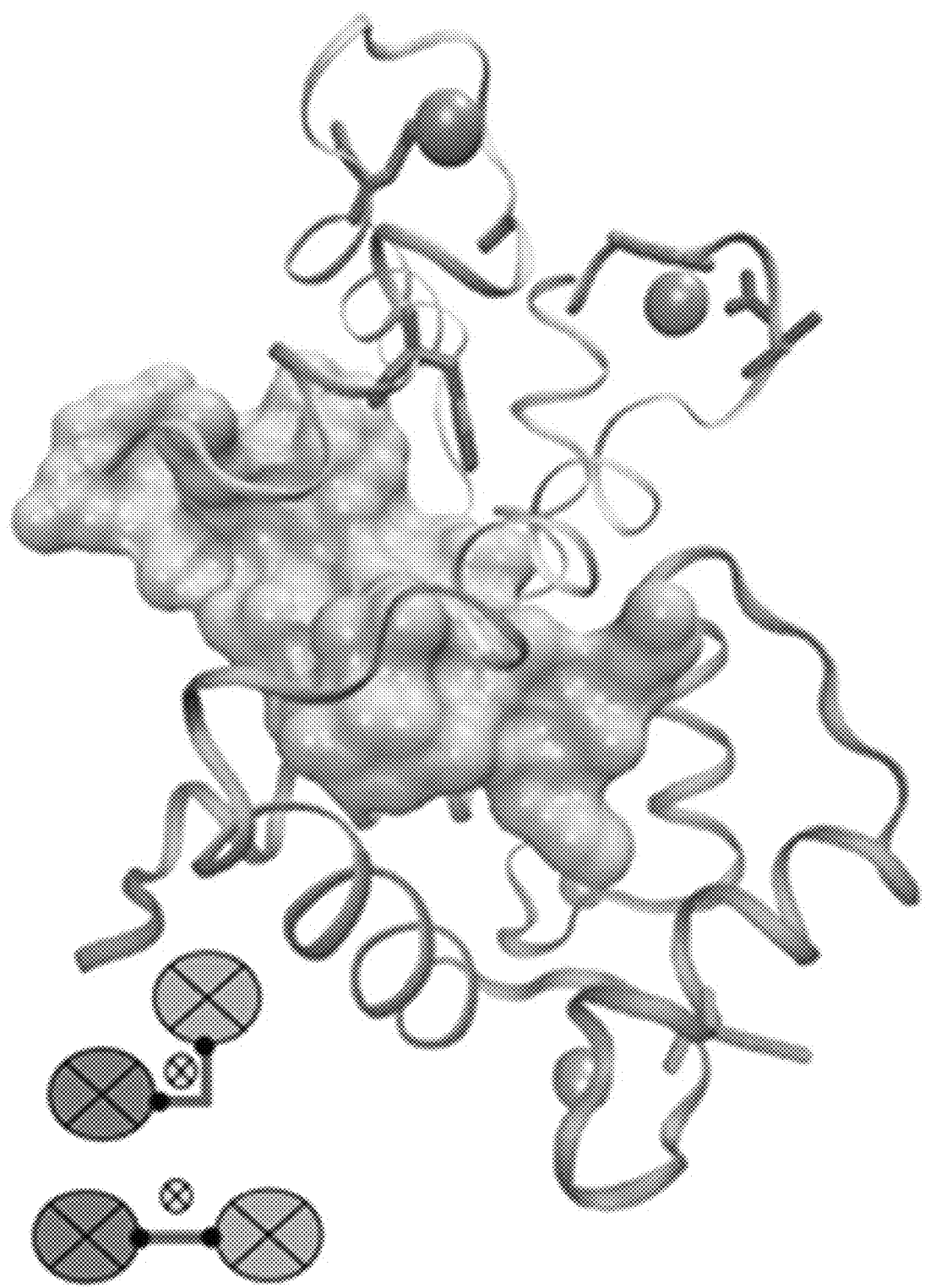
FIGS. 1A and 1B show exemplary simulations using CaM bound to a short peptide representing the IQ domain from L-Type $Ca^{2+}$ channel. (A) The ribbon representation of calmodulin bound to the L-type $Ca^{2+}$ channel IQ domain peptide (PDB: 2F3Y), shows the calcium binding protein in a compact conformation where both the C-lobe (blue) and N-lobe (orange) make contacts with the peptide (yellow). The flexible linker region of calmodulin (red) imparts a high degree of conformational flexibility. (B) The results of molecular dynamics simulations produced consistently compact structures, as measured by the end to end distance of the linker region and the dihedral angle formed by the center of mass of each calmodulin lobe and their respective intersections with the linker region. Variant trajectories showed distinct variation from the wildtype structures.

MD simulations permit the study of the dynamic processes that take place in biological systems, for example, protein stability, protein folding, conformational changes of protein and nucleic acids, and molecular binding including receptor/ligand binding and protein/nucleic acid binding. These studies provide useful information for designing drugs for the treatment of various diseases including cancer and genetic diseases. They also provide information for predicting the severity of a disruption, such as a mutation, to the function of a macromolecule, such as a protein.

To date, there isn't a method that is able to differentiate how different mutations in the same gene can result in completely different phenotypes or traits. Examples of methods to predict how genetic variants can change function include SIFT, PolyPhen2, PROVEAN, CLIMPS, HotMAPS, SpacePAC, HotSpot3D, 3dHotspots, Mutation 3D, and Mechismo. These current methods utilize information in the sequence, such as conservation of homologous sequences or similarity between wildtype and mutant sequences, and information in the structure, such as mapping and analyzing variant amino acids to the static interaction interface of PDB crystal structures to obtain information about the mutation or mutant. Proteins often perform more than a single molecular function through interactions in the cell. The methods only predict whether a mutation will or will not disrupt a single, generalized function. They fail to differentiate between divergent phenotypic changes to function, and they cannot predict the severity of a mutation within multiple phenotypic contexts. As a result, these current prediction methods are severely limited in the type of information they provide about how protein function changes with a mutation.

The present disclosure describes methods for predicting the phenotype caused by a genomic variation, such as a mutation, for providing an accurate diagnosis and treatment and/or management of a disease. The methods described herein are for determining the functional effects, such as functional severity and functional disruptions, caused by one or more variant macromolecules. As is well-known, a variant macromolecule has a different sequence, amino acid sequence or nucleic acid sequence and a change in the macromolecule's sequence can affects both its physical and/or functional properties. Sometimes a single amino acid mutation in a protein can give rise to an inactive protein, which is a huge change in functional activity and can cause a fatal disease in a subject. The methods described herein include mining features from an all atom molecular dynamics (MD) simulation of the one or more variant macromolecules, classifying the features using machine learning algorithms, and ranking the functional effects of the one or more variant macromolecules with respect to the corresponding wildtype macromolecule. The information obtained regarding the functional effects caused by the one or more macromolecules can be ranked based functional severity or functional disruption caused by the mutation relative to the wildtype molecule.

The methods described herein use MD simulations on wildtype and genetic variants to create ensembles of structures and obtain information of how the population of structures of a variant differs from that of the corresponding wildtype. The structures are clustered based on differences in 3-dimensional (3D) organization of structural domains, and features are extracted from these variant specific representations for further analysis by various machine learning methods. The methods described herein use ML to analyze MD simulation data.

In embodiments, the methods described herein include one or more of the following insteps: (1) generating a conformational landscape for mutant protein structures; (2) clustering the structures to identify variant specific populations of protein structure conformations; (3) obtaining and quantifying structural and energetic features of individual structures within each conformational population such as: global structural features, dynamics of subdomains in the structure, energetic interactions, and statistical characteristics of overall collection of structures; (4) using unsupervised clustering of multidimensional feature sets obtained in (3) to identify mutant conformational populations that diverge from those found in the wildtype simulations; (5) performing principle component analysis (PCA) on the multidimensional feature set and collapse the distribution of the wildtype and the divergent variant structures identified in step 4 into a weighted centroid in the principle component space; and (6) using coordinates of the variant centroids in the PCA to obtain information for predicting the specific phenotypic disruption and ranking the severity caused by the mutations as compared to the wildtype.

In step (1), generating the conformational landscape for the wildtype protein and mutant protein using all atom MD simulations includes using any software, any parameter set or force field used to calculate the potential energy, and any protein/ligand interaction system. The parameter sets include rule sets that govern the behavior of individual atoms in the system. The structures generated through MD simulations can be characterized by several metrics for comparing the impact of a mutation on conformational dynamics, for example: global structural features, dynamics of subdomains in the structure, energetic interactions, and statistical characteristics of overall collection of structures. In this step, each mutant or variant can generate approximately 10,000 to 100,000 individual structures, and trajectory refers to all of the structures of a given variant.

Examples of MD simulation software includes Gromacs, NAMD, Amber, and CHARMM. Examples of ligand in a protein/ligand interaction includes an ion, a small molecule, another protein, or a nucleic acid. Examples of nucleic acid includes RNA, DNA, and cDNA. The ligand can also be a substrate, when the mutant protein is an enzyme. The ligand can also be an agonist, an antagonist, an effector molecule, or an antibody.

In step (2), clustering structures obtained from MD simulations to identify variant specific populations of protein structure conformations can be performed based on well-known algorithms, including root mean square deviation (RMSD). For example, the hierarchal clustering based on the pairwise RMSD measured between all structures produced by the MD simulations for individual variant trajectories. The structures generated in step (1) are sorted into clusters based on structure trajectories. Clustering bins the collection of structures of a given variant into multiple groups based on their structural similarity. Therefore, each cluster includes multiple structures, which make up a conformational population.

In step (3), obtaining and quantifying structural and energetic features of individual structures within each conformational population such as one or more of the following feature categories: global structural features, dynamics of subdomains in structure, energetic interactions, and statistical characteristics of overall collection of structures. The structural and energetic features are defined for each individual structure.

Structural features are uniquely defined per gene per family. As an example, for calmodulin, structural features include dihedral angles measured between the 4 points making up the 1 center of mass of the C-lobe, center of mass of the N-lobe, and the two points where each lobe attaches to the linker region. The linker distance for calmodulin is measured by the length between the linker attachment to the C and N lobes. The distance from the center of mass form the C and N lobes to the center of mass of the bound ligand are also measured. Global structural features are measured using the 3D coordinates of each protein structure.

Energetic features include Van der Waals forces, electrostatic forces, and non-bonded energies occurring between the ligand and the protein structure.

The macromolecules can include subdomains, for example, a protruding loop or strand, which may adopt different local dynamics relative to the motion of the overall structure. Thus, dynamics of subdomains in structure can be obtained.

Energetic interactions which refer to the sum of all atomic interactions between the protein and ligand can be obtained.

The features described above are calculated for each of the structures in each of the variant clusters using equations from geometry and biophysics. In embodiments, Visual Molecular Dynamics (VMD) can be used, or a code could be written to perform the calculations.

In step (4), using unsupervised clustering of the multidimensional feature sets to identify mutant structures which diverge from those found in the wildtype simulations. This includes using any unsupervised ML clustering algorithms to define divergent variant structures based on similarity or distance metrics. Examples of such algorithms include hierarchical clustering, k-means, multivariate normal distributions, DBSCAN, and others. The multifunctional feature sets are based on the structural and energetic features described in step (3).

Figure 3A:
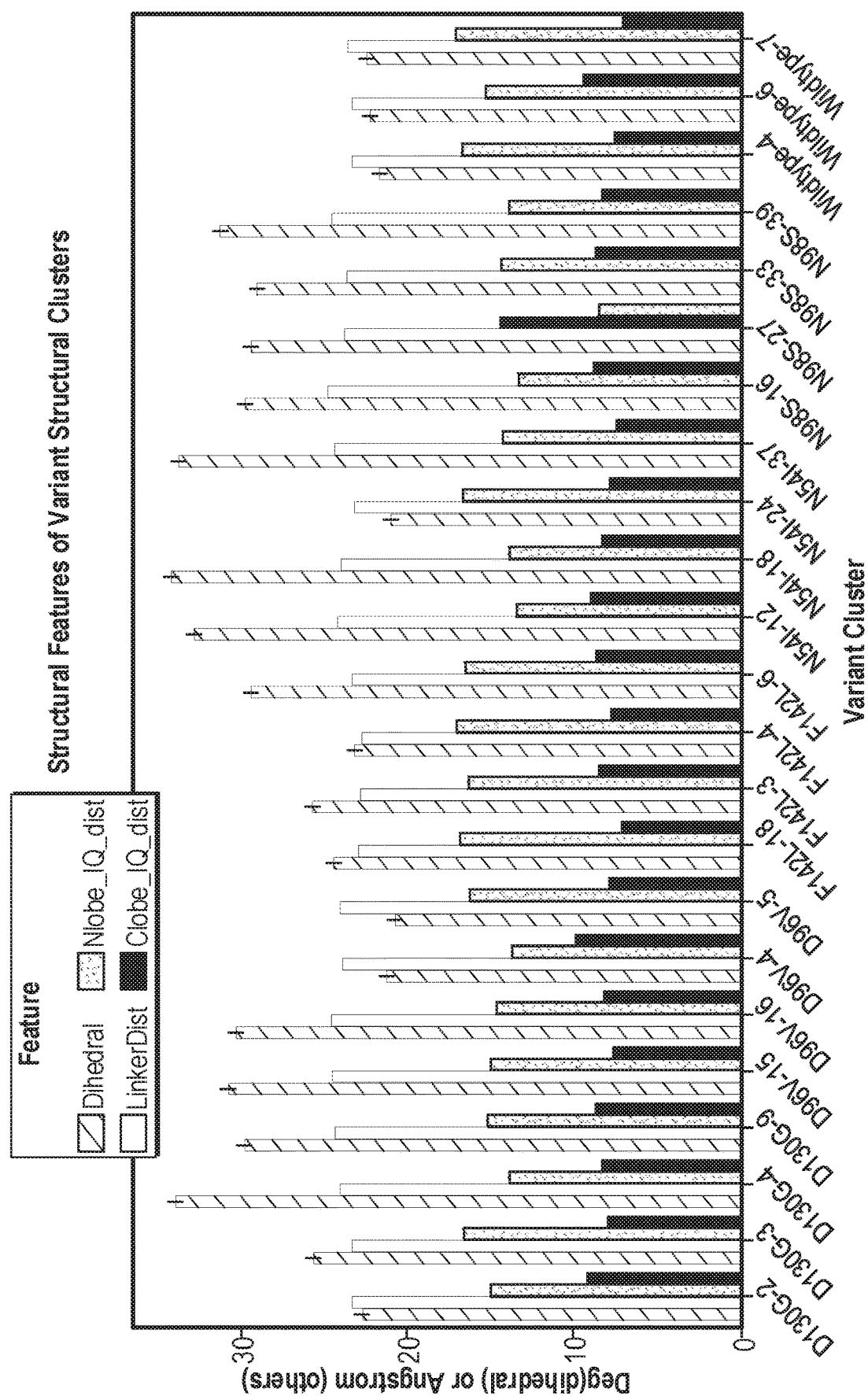
FIGS. 3A-3B show the analysis of clustering of individual variant trajectories. The variant trajectories were used to define several (A) structural and (B) energetic features associated with the variant sub-populations. Variant clusters take on a range of values when compared to other sub-populations and show some overlapping similarities between structures from alternate variant simulations.
Figure 3B:
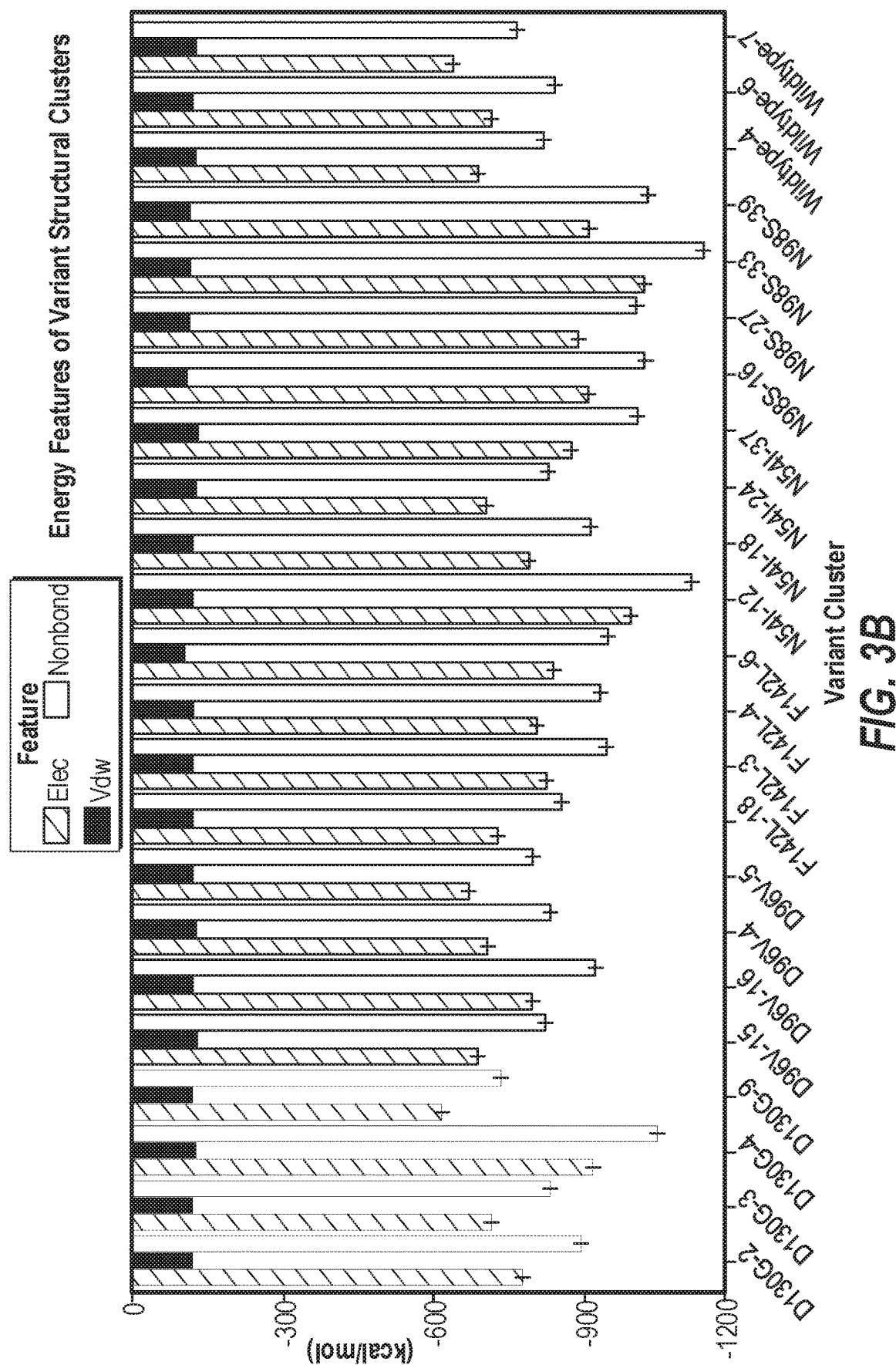

In step (5), performing principle component analysis (PCA) on the multidimensional feature sets includes mapping all structures to a multidimensional plot of the principle components that define the features that characterize and separate the different structures and collapsing the distribution of the wildtype and the divergent variant structures identified in step 4 into a weighted (variant) centroid in the principle component space. PCA is a statistical procedure that uses an orthogonal transformation to convert a set of observations of possibly correlated variables into a set of values of linearly uncorrelated variables called principal components. The number of principal components is less than or equal to the number of original variables. In other words, the PCA is a mathematical transformation of the feature set, which results in a set of principle components (in FIG. 4A, PC1 and PC2). The feature set can include a number of variables. As an example, in FIG. 3 the feature set includes 7 variables. The principle components are determined by the ML from the feature set. There can be more than one measure included in a component. The first component is the group of measure that provides or explains the trend in the data.

In step (6), the coordinates of the variant centroids in the PCA plot are used to predict the specific phenotypic (characteristic, trait, disease) disruption and rank relative severity compared to the wildtype system. In this step, regions of PCA plot correspond to unique phenotypic associations and are defined by the coordinates of variants with a known phenotypic consequence, for example, the variants of similar phenotype cluster together. Moreover, machine learning classification algorithms can be applied to multidimensional feature sets (from step 3) to build a predictive classifier for each phenotype. The relative severity of a phenotypic disruption correlates with the Euclidean distance between the centroid of the wildtype and the centroid of the mutant.

The methods described herein can be used with various macromolecules for providing information for predicting, diagnosing, and treating various diseases. Macromolecules includes proteins, nucleic acids, and polymers. Proteins include phosphoproteins and glycoproteins. Examples of nucleic acids include DNA and RNA. Examples of DNA include cDNA. Examples of RNA include lncRNA, microRNA, and sncRNA. Various diseases include, for example, cancer, neurodegenerative diseases, and genetic diseases. Examples of cancers include breast cancer, ovarian cancer, lung cancer, brain cancer, leukemia, prostate cancer, and pancreatic cancer. Examples of neurodegenerative diseases include Alzheimers, Parkingsons, and Huntingtons.

Genetic diseases include diseases and disorders that are caused by mutations in a single gene (monogenic disease) or in multiple genes (polygenic disease), by a combination of mutations and environmental factors, or by damage to chromosomes (changes in the number or structure of entire chromosomes).

With monogenic diseases, the mutation may be present on one or both chromosomes. Examples of monogenic diseases include Marfan syndrome, Tay-Sachs disease, sickle cell anemia, cystic fibrosis, and polycystic kidney disease. Polygenic diseases are caused by a combination of small inherited variations in multiple genes. Examples of polygenic diseases include cancers, heart diseases, diabetes, and autoimmune diseases.

Chromosome disorders are caused by damages to chromosomes which change the number or structure of the entire chromosome. It could be an excess or deficiency of the genes that are located on the chromosomes. As an example, Down syndrome is caused by an extra copy of chromosome 21 (trisomy 21), while Prader-Willi syndrome is caused by the absence or non-expression of a group of genes on chromosome 15. Chronic myeloid leukemia (CML) may be caused by chromosomal translocation, in which portions of two chromosomes, chromosomes 9 and 22, are exchanged. Although no chromosomal material is gained or lost, a new abnormal gene is formed that leads to the formation of cancer.

Long QT syndrome (LQTS) is a disorder of cardiac repolarization characterized by a prolonged QT interval on electrocardiogram (ECG). In the past, LQTS was referred to as a monogenic disorder, but it recently has been reported that it can be a polygenic disorder as well.

Catecholaminergic Polymorphic Ventricular Tachycardia (CPVT) is an inherited disorder that is characterized by an abnormal heart rhythm. When the heart rate is increased in response to physical activity or emotional stress, it can trigger an abnormally fast and irregular heartbeat, ventricular tachycardia.

Although both LQTS and CPVT can cause sudden death in young adults and children as a result of the sudden cardiac arrhythmia, these disorders are sometimes treatable if correct diagnosis are made.

Recently, mutations in calmodulin have been associated with a number of disease-causing mutations. Calmodulin is a multifunctional intermediate calcium-binding messenger protein expressed in all eukaryotic cells. It is an intracellular target of the secondary messenger Ca2+, and the binding of Ca2+ is required for the activation of calmodulin. Once bound to Ca2+, calmodulin acts as part of a calcium signal transduction pathway by modifying its interactions with various target proteins such as kinases or phosphatases. Calmodulin (CaM) is a key protein involved in many calcium regulatory processes in cells in many different tissues throughout the body including heart and brain. In particular, CaM variants have been found to give rise to different potentially fatal cardiac arrhythmias CPVT [19-32] and LQTS [29, 33]. Correct diagnosis is a key to disease management.

CaM is a cytoplasmic protein that has 149 amino acids and acts to regulate a number of calcium dependent processes in the cell. Four $Ca^{2+}$ binding, EF-hand domains are evenly distributed into two globular lobes joined by a flexible linker helix, which allows for enormous conformational variability. Not only are the two lobes able to twist with respect to each other, but the collapse of the central linker allows the two lobes to come together and form a compact structure. The conformational dynamics is regulated by binding calcium ions and interacting protein targets and allows for a wide range of calcium dependent regulatory functions. CaM is ubiquitous in eukaryotes and has a conserved sequence across all vertebrates. With hundreds of protein regulatory targets and cooperative calcium binding affinities across a wide range of physiological $Ca^{2+}$ concentrations, there are numerous mechanisms where CaM binding contributes to stabilizing functional conformations of protein interaction partners [34].

In the cardiac myocyte, CaM plays a crucial role in regulating the coupling of cell excitation to contraction (ECC). This coupling occurs at the diad, a specialized subcellular structure where L-type $Ca^{2+}$ channels ($Ca_V1.2$) on the cell membrane are physically located across from arrays of calcium sensitive ryanodine receptor 2 (RYR2) on the terminal cisterna of the sarcoplasmic reticulum. In response to depolarization, voltage gated $Ca_V1.2$ opens to allow the influx of extracellular calcium into the small volume of the diad subspace. The increase in local $Ca^{2+}$ concentration triggers the opening of RYR2 channels, amplifying the calcium signal in a process known as calcium-induced calcium release (CICR) thereby activating the contractile machinery. The spike in $Ca^{2+}$ also regulates the CaM dependent inactivation (CDI) of $Ca_V1.2$, attenuating $Ca^{2+}$ entry as the cardiac myocyte resets for the next excitation cycle. The functional impairment of proteins involved in both ECC and CICR mechanisms will increase the risk of arrhythmia, as is the case in Long QT Syndrome (LQTS) and Catecholaminergic Polymorphic Ventricular Tachycardia (CPVT). Novel, single missense mutations in CaM have been associated with LQTS and CPVT phenotypes, highlighting the sensitivity of CaM regulatory function to changes in the sequence.

Structurally, CaM binds to a cytoplasmic IQ domain $Ca_V1.2$ even at low concentrations. Upon $Ca^{2+}$ binding, conformational changes in CaM induce channel closing at increased rates compared to thermodynamic or transmembrane voltage processes. A leading mechanistic hypothesis of CaM dependent inactivation involves dissociation of the CaM N-lobe from the IQ domain upon increasing $Ca^{2+}$ concentrations and the subsequent binding to the cytoplasmic $Ca_V1.2$ NSCaTE domain. Presumably, the linking of these two domains by $Ca^{2+}$ bound CaM imparts a mechanistic force on the channel to promote a closed conformation [35].

Recently, several missense mutations in the CaM amino acid sequence have been identified in patients with cardiac arrhythmia [19-27]. Further investigation shows that some variants disrupt calcium binding and alter CDI of the L-Type $Ca^{2+}$ channel, leading to the LQTS phenotype. Other variants affect CaM interactions with other important proteins involved in ECC, including binding to RYR2 and sodium channels, the former resulting in altered cardiac myocyte functions associated with CPVT. Predicting the potential for a specific variant to have a physiological consequence is a major challenge in the age of high throughput sequencing, especially in diseases that arise from subtle changes to molecular interactions. Experimental evaluation of all potential variants is intractable, but as the study shows, advanced computational analysis enables the a priori prediction of the functional impact of genomic variation.

As an example, the methods described herein used variants associated with distinct arrhythmia mechanism (CPVT and LQTS) were selected that not only resolve between the phenotypes, but also reflect the observed severity of the disease. Specifically, unsupervised clustering of the variant features sets in principal component space identified variant structures that overlap wildtype and other structure that uniquely diverge from wildtype. PCA of the simulation derived feature sets were then used to map the variant structures to the feature space defined by PC1 and PC2. Variant structures overlapping with the wildtype conformations are removed and the remaining variant structures were collapsed into a weighted centroid. The centroids for variants causing a specific phenotype separated into distinct regions of the principle component feature space, and furthermore, the Euclidean distance between the wildtype and variant centroid correlate to the severity of the phenotype observed through experiments.

In summary, modeling the conformational dynamics in the folded structure of CaM variants provides insight into the severity of functional disruption by comparing changes in structural metrics and energetic interactions with the wildtype structure. Using all atom molecular dynamic simulations of CaM bound to the IQ domain of the L-Type $Ca^{2+}$ channel, features of variant specific conformational diversity were used to measure the impact of three LQTS associated variants (D96V, D130G, and F142L) and two associated with CPVT phenotypes (N54I, N98S) on CaM structural interactions.

The methods described herein can be used to identify the phenotype, trait, or disease caused by a genetic variant. As an example, the methods can be used to obtain information with respect to the interaction of an agent with a macromolecule. An agent can be a drug, a chemical, a pesticide, or an antibiotic. The method can be used to define the interaction of the agent with the macromolecule, whether a protein or a nucleic acid variant, to determine drug resistance or antibiotic resistance.

The methods described herein can be used to determine the phenotype of a nucleic acid variant based on protein binding to the nucleic acid variant, such as transcription factor binding. In this case, phenotype refers to how the protein-nucleic interaction is measured. For example, protein binding to nucleic acid variant regulates expression of genes that can differ depending on the protein variant which results in certain phenotype or trait. Previous studies have linked diseases such as pancreatic cancer, type 2 diabetes, myelodysplastic syndrome, and idiopathic pulmonary arterial hypertension to mutations in promoter region DNA [45, 46].

Similarly, the methods described herein can also be used to determine the phenotype of a protein variant based on nucleic acid binding to the protein variant, such as histone binding. The phenotype in this case, for example, could be the regulation or expression of a gene i.e. the accessibility of the gene for transcription. The following are examples of transcription factor protein mutation that are associated with a disease: Pit-1 mutations have been associated with pituitary hormone deficiency, Brn-4 have been linked with X-linked deafness, PAX-3, PAX-2, and PAX-6 mutations have been linked with Waardenburg syndrome, colobomas of the optic nerve and renal hypoplasia, and eye defects, respectively [47, 48, 49].

The methods described herein can be used to obtain information regarding the conformational changes, stability, folding, unfolding of a macromolecule, for example a protein. As an example, the obtained information could be used for comparing a wildtype protein with a variant protein to determine the effects of the variant protein. The information also could be used to determine a protein's interaction with a candidate drug or any other small molecule to provide information for treatment or management of a disease that a subject is suffering.

The present disclosure also describes a computer system for implementing the methods described herein. A computer system is an apparatus or device including one or more processors, a memory, input/out interface, and a network interface. The memory is communicatively coupled with the one or more processors. The one or more processors are configured to execute computer program instructions for implementing the methods described herein. The computer program instructions are stored on and/or provided by the memory. Examples of computers include personal computers, laptops, computer clusters, supercomputers, and any other kind of computer.

The memory includes a plurality of components including data structures and one or more program modules. The data structures include structural data of macromolecules and ligands stored in the memory. The one or more program modules stored in the memory can include a program for performing MD simulation to obtain a conformational landscape for the wildtype and mutant macromolecules, a program for clustering to identify variant specific populations, a program for obtaining and quantifying features of the structures including structural and energetic features, a program for clustering of multidimensional feature sets using ML to identify mutant conformational populations that diverge from the wildtype, a program for performing PCA on the multidimensional feature set, and a program for using the variant centroids in the PCA plot to obtain the specific phenotypic disruption and rank them relative to the wildtype.

Memory is an example of computer-readable medium. It may include volatile storage devices in computer-readable media, random access memory (RAM), and/or non-volatile memory, such as read-only memory (ROM) or flash memory (flash RAM). Computer-readable media include permanent and non-permanent and removable and non-removable media. Computer-readable commands, data structures, program modules are examples of information stored on the computer-readable media. Examples of computer storage media include phase-change memory (PRAM), static random access memory (SRAM), dynamic random access memory (DRAM), other types of random access memory (RAM), read-only memory (ROM), flash memory, compact disk read-only memory (CD-ROM), digit multifunction disc (DVD), and magnetic tape. Computer-readable media does not include temporary or transitory computer-readable media, such as modulated data signals and carrier waves.

The computer processors include a plurality of components including, multicore CPUs, multi-CPU computers and computer clusters, many-core CPUs, general purpose graphical processor units (gpGPUs), and other computer processors.

In embodiments, the methods described herein are performed using computer processors of sufficient computational power to perform the simulations and analysis. Currently molecular simulation and machine learning are done on parallel architectures such as multi-core CPU, multi-CPU systems, and general-purpose GPUs. In embodiments, the computer system for performing the methods described herein includes memory sufficient for the calculations and storage such as disks, disk arrays, solid state drives (SSDs) with speed sufficient for the simulations and analysis.

Variants and mutants are used interchangeably to mean genes or proteins with mutations. For examples, genes that have a nucleic acid sequence that differs from the corresponding wildtype gene is a variant or mutant gene. Proteins that have an amino acid sequence that differs from the corresponding wildtype protein is a variant or mutant protein.

Methods described herein include predicting, diagnosing, and treating subjects (humans, veterinary animals (dogs, cats, reptiles, birds, etc.), livestock (horses, cattle, goats, pigs, chickens, etc.), and research animals (monkeys, rats, mice, fish, etc.). Subjects in need of a treatment or diagnosis (in need thereof) are subjects that are suffering from a disease, are experiencing symptoms of a disease, or at high risk of developing the disease.

Methods described herein are also useful for identifying traits in agriculture such as plants and livestock.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The following exemplary embodiments and examples illustrate exemplary methods provided herein. These exemplary embodiments and examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

Exemplary Embodiments

The following are exemplary embodiments:
1. A method for determining the functional effects of one or more variant macromolecules, wherein the method comprises mining features from all atom molecular dynamics (MD) simulations of the one or more variant macromolecules, classifying the features using machine learning algorithms, and ranking the functional effects of the one or more variant macromolecules with respect to the corresponding wildtype macromolecule.
2. The method of embodiment 1, wherein the one or more variant macromolecules are variant proteins.
3. The method of embodiment 1 or 2, wherein the one or more variant macromolecules cause a disease.
4. The method of any one of embodiments 1-3, wherein the one or more variant macromolecules cause a genetic disease.
5. The method of any one of embodiments 1-4, wherein the genetic disease is Long QT Syndrome or Polymorphic Ventricular Tachycardia.
6. The method of any one of embodiments 1-5, wherein the method includes generating a conformational landscape for the one or more variant proteins and the corresponding wildtype protein using all atom MD simulations.
7. The method of any one of embodiments 1-6, wherein the method includes clustering structures to identify variant specific populations of protein structure conformation.
8. The method of any one of embodiments 1-7, wherein the method includes using root mean square deviation to cluster structures.
9. The method of any one of embodiments 1-8, wherein the method includes quantifying structural and energetic features of individual structures within each conformational population.
10. The method of any one of embodiments 1-9, wherein the method includes using unsupervised clustering of multidimensional feature sets (consisting of structural and energetic features) to identify mutant conformational populations which diverge from those found in the wildtype simulations, thereby identifying divergent variant structures.
11. The method of any one of embodiments 1-10, wherein the method includes performing principle component analysis (PCA) on the multidimensional feature sets.
12. The method of any one of embodiments 1-11, wherein the results of PCA for the individual distributions of wildtype and divergent variant structures are collapsed into a weighted variant centroid in the principle component space.
13. The method of any one of embodiments 1-12, wherein the method includes using the weighted centroid in the PCA plot to determine the specific phenotypic disruption and rank relative functional effect of the one or more variant proteins with respect to that of the corresponding wildtype protein.
14. The method of any one of embodiments 1-13, wherein the ranking of the functional effect of the one or more variant proteins provides information for distinguishing disease phenotypes caused by the one or more variant proteins.
15. The method of any one of embodiments 1-14, wherein the functional effect is functional severity caused by the one or more variant macromolecules.
16. The method of any one of embodiments 1-15, wherein the method includes determining the functional effects of the one or more variant macromolecules with respect to binding to a ligand.

17. The method of embodiment 16, wherein the ligand is an ion, a small molecule, a protein, or a nucleic acid.
18. The method of embodiment 16 or 17, wherein the one or more variant macromolecules are variants of an enzyme and the ligand is a substrate.
19. The method of any one or embodiments 16-18, wherein the variant macromolecules are nucleic acids and the ligand is a nucleic acid binding protein.
20. The method of any one or embodiments 16-19, wherein the method provides information for designing a drug for treatment of a disease.
21. The method of any one of embodiments 1-20, wherein the method is a computer implemented method.

Examples

Introduction

Variation in genomic sequences are thought to confer traits or underlie genetic diseases through subtle changes to the protein conformational dynamics and subsequent molecular interactions that drive complex biological systems. Breakthroughs in sequencing technology has made the identification of variants faster and more cost-effective and have resulted in the discovery of many new variants [1]. Rare variants underlie many complex diseases, are abundant in the population, and are geographically localized [2]. However, many more variants remain unclassified. Moreover, due to their rarity, large sample size or improved methods will be required to associate these variants with complex traits and disease [3]. As a result, one of the largest unsolved challenges in biology is the prediction of the effect of genomic variation on altering the phenotype i.e., the traits of an organism or the role of variants in disease [4-8].

This represents a challenge facing the genomics community at large: accurately predicting the specific functional impact of a given variant has enormous implication on genomic analysis and therapeutic decisions. Although previous molecular simulation studies have shown that genetic variants have structures different from wildtype proteins and combined molecular simulation and docking studies predict that variants have different drug binding affinities [9-11], the analysis methods fall short of predicting/ranking a variants relative functional impact.

To address this pressing need, a method that leverages machine learning to identify and quantify features of all atom simulations to predict the specific effect and disruptive severity of genetic variants on molecular function. All atom simulations are widely used in to understand the function of proteins and how variation can impact structure [12-16]. However, their transformative impact on clinical translational has yet to be demonstrated. Machine learning approaches has garnered much attention recently by its ability to differentiate between inputs [17, 18]. By mining features from these simulations and using machine learning to classify them, this method can differentiate between different diseases caused by genomic variation in a particular protein and predict rank the disease severity of multiple variants resulting in the same disease phenotype.

In this study, it is shown that features extracted from all atom simulations of LQTS and CPVT associated variants in CaM can distinguish the nature and severity of functional disruption. Metrics describing the global structural conformations and energetic contributions to molecular interactions can identify a variant specific divergence from the wildtype dynamics, which correlate with severity of functional disruption in CaM dependent processes regulating calcium dynamics in cardiac myocytes [27]. More broadly, the results highlight the potential for extracting structural and energetic features from molecular dynamics simulations as features for more advanced machine learning classification algorithms.

Methods.

For all the molecular dynamics (MD) simulations, the structure of wildtype $Ca^{2+}$ CaM bound to the IQ domain of the L-Type $Ca^{2+}$ channel (PDB: 2F3Y) was used. Since the LQTS (D96V, D130G, F142L) mutations disrupt calcium binding in regions of their respective EF-hand domains in the C-lobe, the corresponding ion was removed from the variant structure [36]. The Mutator plug-in for Visual Molecular Dynamics (VMD) [40] was used to mutate the appropriate residue. All $Ca^{2+}$ ions were left in the CPVT (N54I, N98S) variant, since those residues do not directly interact with $Ca^{2+}$. The five variants and wildtype structures were solvated in a water box and the system was neutralized using the Solvate and Autoionize plugins for VMD [40]. The MD simulations were carried out using the GPU-enabled implementation of Nanoscale Molecular Dynamics (NAMD) [41] employing CHARMM36 force field and producing for each variant of CaM three 200 ns trajectories at 310 K [42]. Periodic boundary conditions were used, and structures were saved every 10 ps. The results were processed in VMD, first using the pcbtools plug-in to unwrap the structure trajectories [40].

The structures generated through the MD simulations were characterized by several metrics to compare the impact of the mutations on the conformational dynamics. The end-to-end distance between the linker termini provides a measure of the distance between CaM lobes. A measure of the relative orientation of the N-lobe and C-lobe is obtained by measuring the dihedral angle formed by the end points of the linker region and the centers of mass of each CAM lobe. Additionally, a crude measure of the tightness of binding was determined by measuring the distance from the center of each lobe to the center of the IQ peptide. The non-bonded energies between CaM and the IQ peptide were calculated with the NAMD Energy plugin in VMD [40].

To identify variant specific structural populations, clustering was performed based on the root mean squared deviation (RMSD) of the CaM structures when aligned by the IQ peptide. Hierarchal clustering of the pairwise structural similarity produced distinct populations through selection of a clustering threshold which maximized the number of clusters which contain at least 10% of the overall trajectory, where the sum of populated clusters must exceed 50%.

Visualization of conformational features, and PCA was carried out using R [43, 44]. Variant centroids were calculated by first removing sub-populations most similar to wildtype, as defined through hierarchal clustering. The remaining variant clusters were combined in the PC feature space, where centroids of sub-population clusters where merged to an overall variant centroid, weighted according to its proportion of the overall trajectory conformations. The distance between centroids was calculated as a Euclidean distance.

Example 1

The simulations were initiated using the experimentally determined structure of wildtype CaM bound to a short peptide representing the IQ domain from the L-Type $Ca^{2+}$ channel [36] (FIG. 1A). In this initial structure, a compact CaM is wrapped around the α-helical IQ peptide with both the N-lobe and C-lobe forming intermolecular interactions.

Three 200 ns simulation trajectories were used to sample the conformational landscape. In the course of simulations, neither CaM lobe dissociated from the IQ peptide, nor RMSD has deviated by more than 5 Å from the wild-type structure (not shown).

Figure 1B:
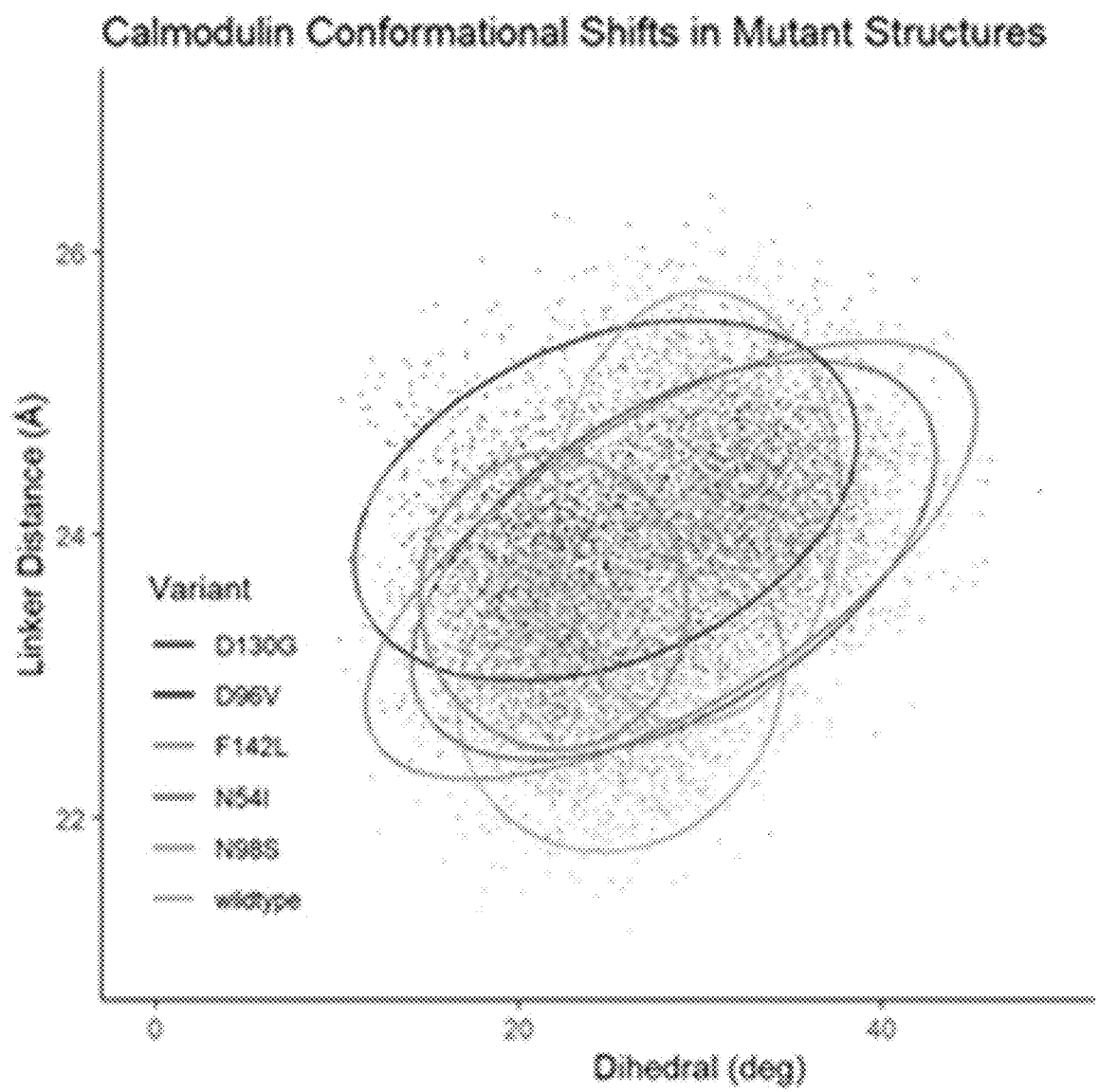

The subtle structural variation induced by CaM mutations is captured by metrics relating the relative positions of the N- and C-lobes, which include the linker distance and the relative twist of the N- and C-lobes (see Methods for their definitions). These metrics have been used in previous molecular dynamics simulations to characterize variant induced changes to CaM conformational dynamics [37]. FIG. 1B shows the conformational distribution of CaM variants overlap, revealing their uniquely distributed conformational profiles. In the case of the LQTS mutations, the divergence of a particular variant from the wildtype distribution approximates the severity of functional disruption of CDI observed single cell experiments, where functional impairment of F142L being less severe than D130G or D96V [27].

Example 2

Figure 2A:
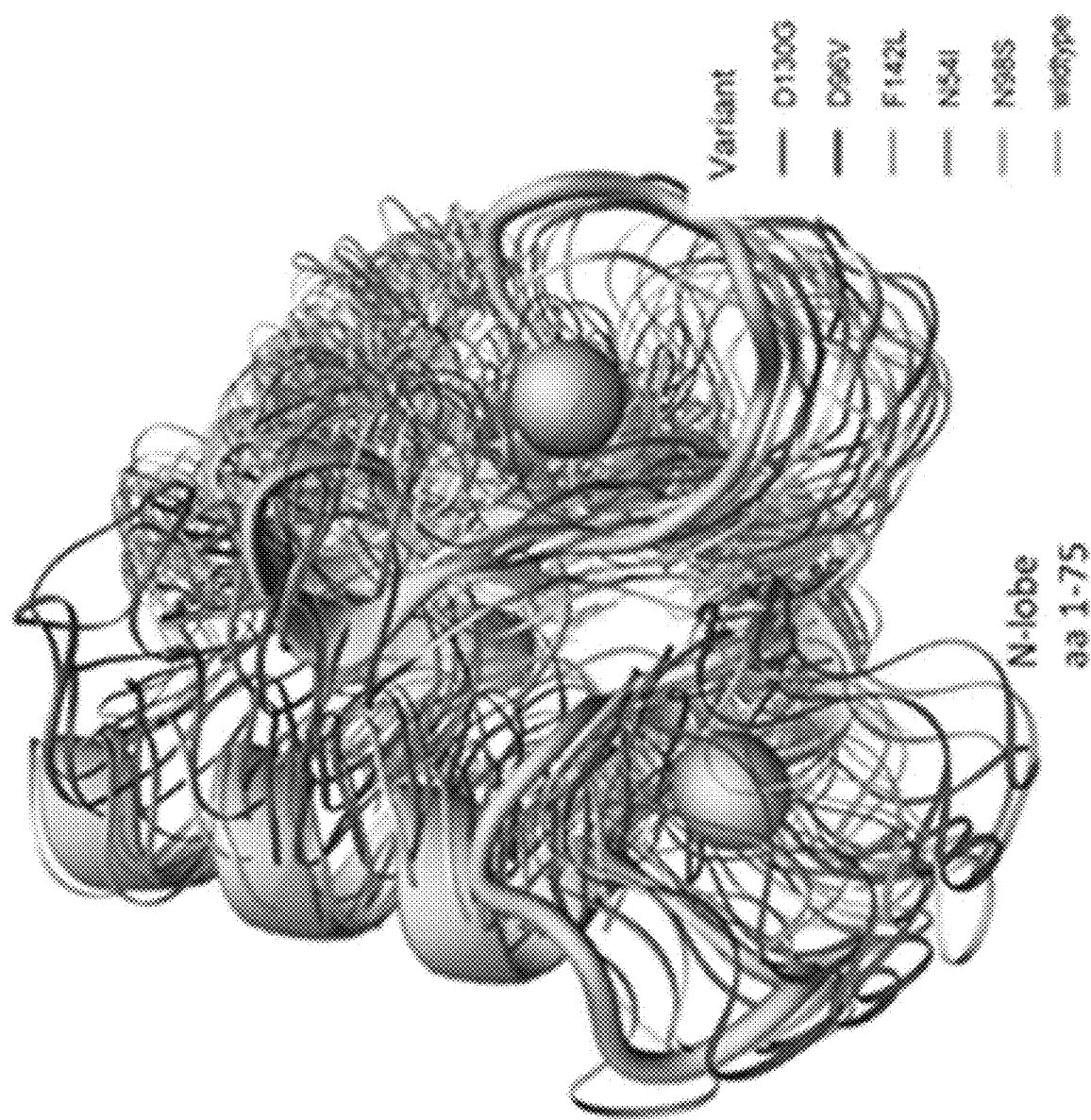
Figure 2C:
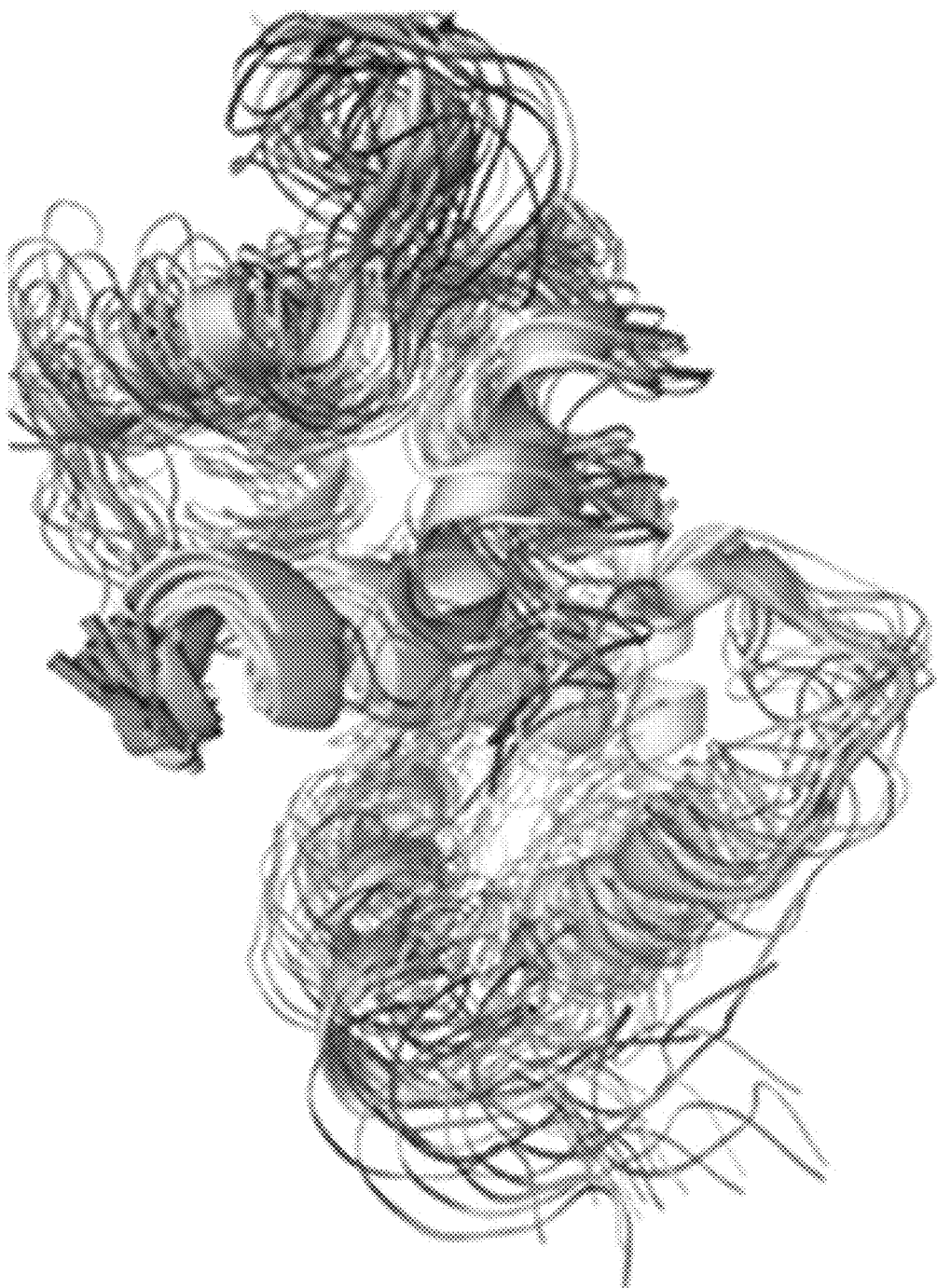

The conformational distributions captured by the two measures are not always sufficient to distinguish between functional differences, as illustrated by the overlap of the LQTS variant D130G with CPVT variant N54I. While all variants show a decreased affinity for RYR2 [27, 38], the N54I variant does not impair CDI [27]. The distribution of the N98S variant shows significant overlap with other variants, but how the unique population level profile translates to a more severe CPVT phenotype than the other variants is unclear [38]. Molecular scale structural comparisons alone are not enough to discriminate between the subtle functional differences, but structural clustering of individual variant trajectories revealed sub-populations with distinct changes to local structure (FIG. 2). The analysis of these clusters through the definition of several distinct population features (FIG. 3) reveals large variation within individual variant clusters and between the overall distributions of individual variants.

Example 3

Figure 4A:
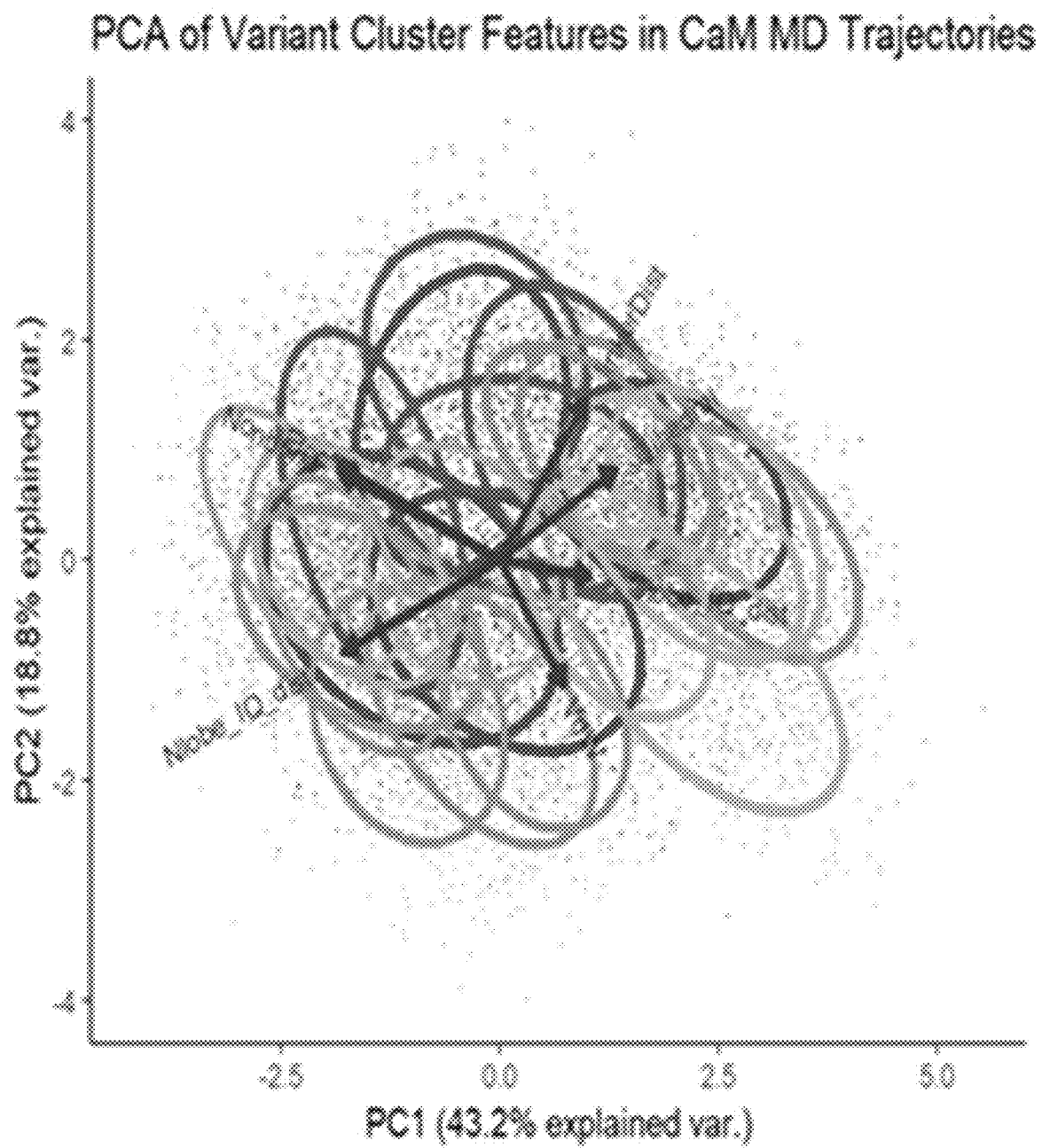
FIGS. 4A-4C show distinct separation of certain conformational sub-populations. (A) Principle component analysis of the structural and energetic features show both separation and overlap of variant sub-populations with those derived from the wildtype simulations. When the (B) overlapping variant populations are removed and the variant distributions are (C) collapsed into a weighted centroid, the separation from the wildtype centroid correlates with the observed functional impairment of calcium dynamics in LQTS variants (D130V>D96V>>F142L) [27]. The separation of the CPVT variants from the LQTS mutation could indicate alternate functional changes. The separation of the CPVT variants (N98S>N54I) also correlates with the severity of the defect [38].
Figure 4B:
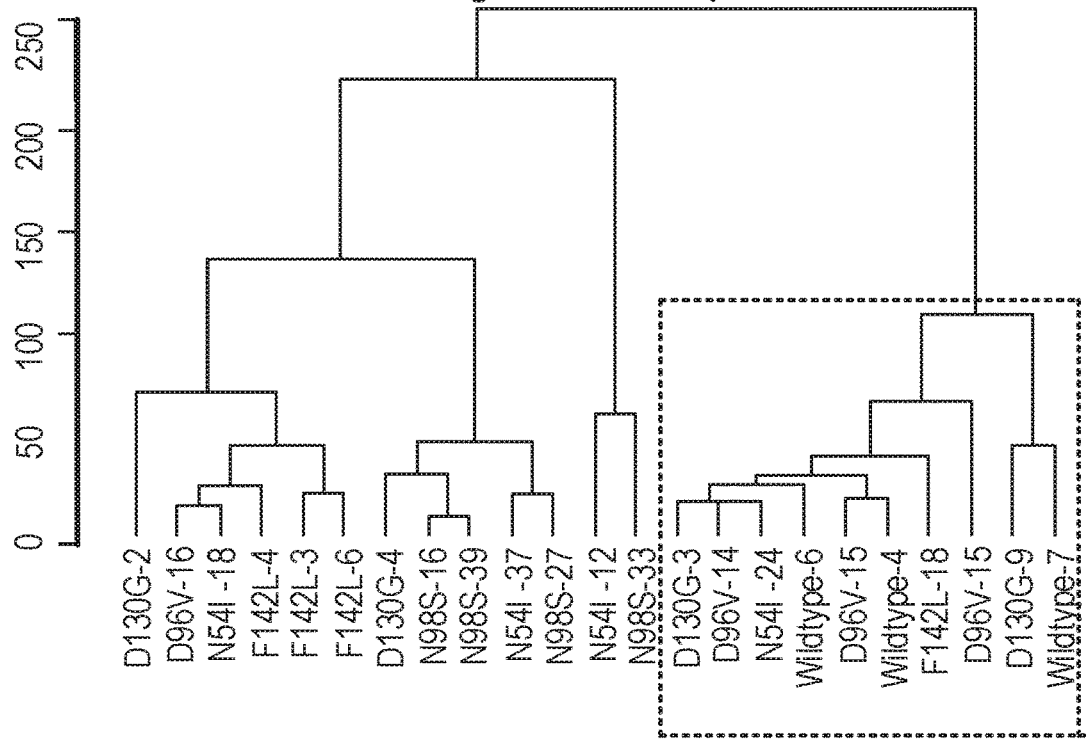
Figure 4B:
Figure 4C:
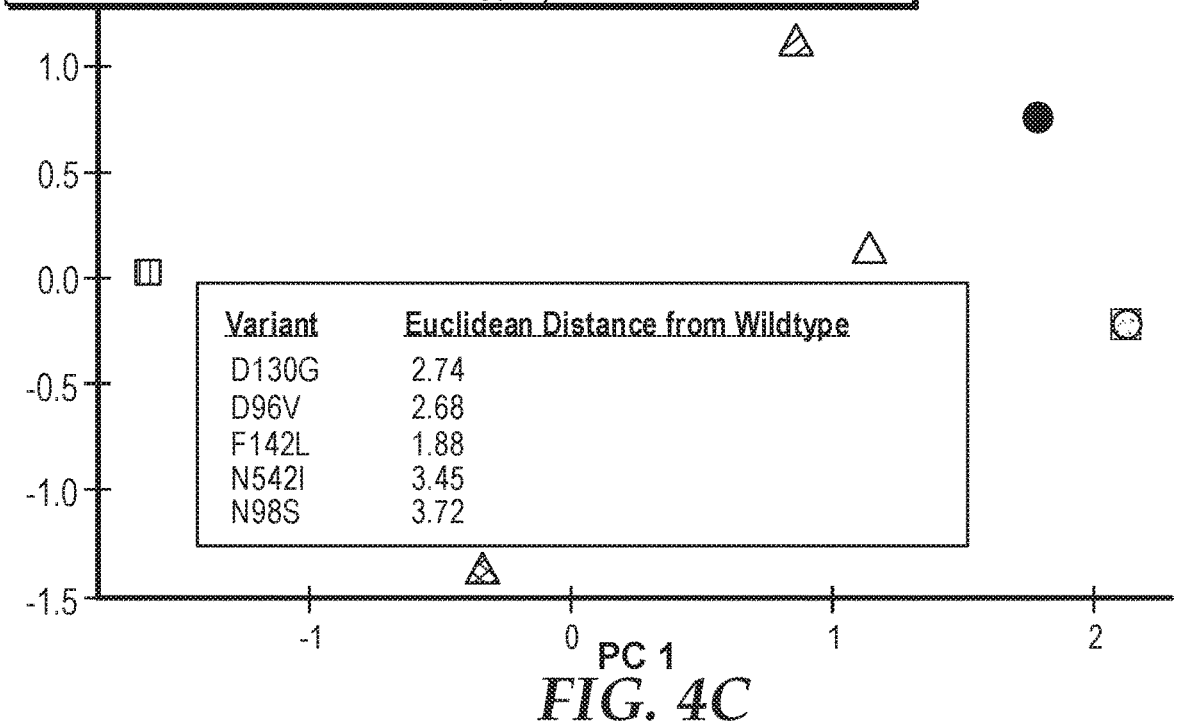

The complexity of the conformational profiles lends itself to multivariate analysis and plotting the first two principle components of the variant trajectory structures shows distinct separation of certain conformational sub-populations (FIG. 4A). Clearly, the distributions more fully distinguish between the variant specific conformational profiles than molecular scale structural attributes alone. Furthermore, if variant clusters which share similar features to the wildtype are removed (FIG. 4B), the centroids of the remaining variant structures collapse into distinct and informative regions of the principle component feature space (FIG. 4C). The Euclidean distance of each centroid for the LQTS and CPVT mutants are separate and each follows the relative impact on $Ca^{2+}$ transient dynamics in cardiac myocytes [27, 38]. It should be noted that while the distribution multivariate feature space is capturing interactions with the L-Type $Ca^{2+}$ channel peptide, the distribution of variant centroids may also contain information related to similar CaM interactions, such as the CDI of voltage gated $Na^+$ channels which maintain ionic homeostasis and contribute to arrhythmogenic mechanisms [39].

An additional feature of the principle component analysis is a measure of individual feature contributions to the first two principle components. This insight into the nature of functional disruption can be used to further the understanding of divergent systematic impacts of variation. For example, D130G and F142L both lose calcium binding at the same EF hand, but divergence from the wildtype conformational distribution shows the underlying driven by differences in the van der Waals interactions. Another example is the difference in the distance of the N-lobe to the IQ domain, which characterizes wildtype divergent structural populations in most variants, which is notable since all sequence mutations occur in the C-lobe and highlight the intricate internal dynamics of CaM which propagates the structural change to more distance regions of the interacting complex.

CONCLUSION

Leveraging machine learning to analyze molecular dynamics simulation trajectories distinguishes between changes in conformational populations of variant structures by increasing the number and source of descriptive features and using more advanced classification methods. It makes the prediction of the functional severity of genomic variants possible in silico with the ability to differentiate between different disease phenotypes, as demonstrated above. This method has applications outside of this specific protein and physiological system. Whether investigating underlying mechanisms for other complex genomic diseases, or optimizing therapeutic approaches to drug resistant somatic variation, leveraging the power of advanced computational analysis is necessary to deconvolute the complexity of the underlying molecular interactions. Extracting structural and energetic features from molecular dynamics simulations and applying a machine learning approach to characterize the difference from the wildtype conformational landscape, can address challenges facing both basic and translational investigators.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The subject matter described above is provided by way of illustration only and should not be construed as limiting. Various modifications and changes may be made to the subject matter described herein without following the example embodiments and applications illustrated and described, and without departing from the true spirit and scope of the present disclosure, which is set forth in the following claims.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

1. Pennisi, E., *Breakthrough of the year. Human genetic variation.* Science, 2007. 318(5858): p. 1842-3.
2. Nelson, M. R., et al., *An abundance of rare functional variants in 202 drug target genes sequenced in 14,002 people.* Science, 2012. 337(6090): p. 100-4.
3. Tennessen, J. A., et al., *Evolution and functional impact of rare coding variation from deep sequencing of human exomes.* Science, 2012. 337(6090): p. 64-9.
4. Jelier, R., et al., *Predicting phenotypic variation in yeast from individual genome sequences.* Nat Genet, 2011. 43(12): p. 1270-4.
5. Botstein, D. and N. Risch, *Discovering genotypes underlying human phenotypes: past successes for mendelian disease, future approaches for complex disease.* Nat Genet, 2003. 33 Suppl: p. 228-37.
6. Rehm, H. L., *A new era in the interpretation of human genomic variation.* Genet Med, 2017. 19(10): p. 1092-1095.
7. Dewey, F. E., et al., *Clinical interpretation and implications of whole-genome sequencing.* JAMA, 2014. 311 (10): p. 1035-45.
8. Posey, J. E., et al., *Resolution of Disease Phenotypes Resulting from Multilocus Genomic Variation.* N Engl J Med, 2017. 376(1): p. 21-31.
9. N, N., et al., *Analysing the Effect of Mutation on Protein Function and Discovering Potential Inhibitors of CDK4: Molecular Modelling and Dynamics Studies.* PLoS One, 2015. 10(8): p. e0133969.
10. Pirolli, D., et al., *Insights from molecular dynamics simulations: structural basis for the V567D mutation-induced instability of zebrafish alpha-dystroglycan and comparison with the murine model.* PLoS One, 2014. 9(7): p. e103866.
11. Swetha, R. G., S. Ramaiah, and A. Anbarasu, *Molecular Dynamics Studies on D835N Mutation in FLT3—Its Impact on FLT3 Protein Structure.* J Cell Biochem, 2016. 117(6): p. 1439-45.
12. O'Connor, M., et al., *Sampling molecular conformations and dynamics in a multiuser virtual reality framework.* Sci Adv, 2018. 4(6): p. eaat2731.
13. Klein, M. L. and W. Shinoda, *Large-scale molecular dynamics simulations of self-assembling systems.* Science, 2008. 321(5890): p. 798-800.
14. Bharadwaj, V. S., et al., *Different Behaviors of a Substrate in P450 Decarboxylase and Hydroxylase Reveal Reactivity-Enabling Actors.* Sci Rep, 2018. 8(1): p. 12826.
15. Moffett, A. S., et al., *Molecular dynamics simulations reveal the conformational dynamics of Arabidopsis thaliana BRI1 and BAK1 receptor-like kinases.* J Biol Chem, 2017. 292(30): p. 12643-12652.
16. Hakala, M., et al., *Molecular mechanism for inhibition of twinfilin by phosphoinositides.* J Biol Chem, 2018. 293(13): p. 4818-4829.
17. Jordan, M. I. and T. M. Mitchell, *Machine learning: Trends, perspectives, and prospects.* Science, 2015. 349 (6245): p. 255-60.
18. Ghahramani, Z., *Probabilistic machine learning and artificial intelligence.* Nature, 2015. 521(7553): p. 452-9.
19. Nyegaard, M., et al., *Mutations in Calmodulin Cause Ventricular Tachycardia and Sudden Cardiac Death.* American Journal of Human Genetics, 2012. 91: p. 703-712.
20. Crotti, L. and e. al, *Calmodulin mutations associated with recurrent cardiac arrest in infants.* Circulation, 2013. 127(9): p. 1009-1017.
21. Makita, N., et al., *Novel calmodulin mutations associated with congenital arrhythmia susceptibility.* Circ Cardiovasc Genet., 2014. 7(4): p. 466-74.
22. Marsman, R., et al., *A mutation in CALM1 encoding calmodulin in familial idiopathic ventricular fibrillation in childhood and adolescence.* Journal of the American College of Cardiology, 2014. 63(3): p. 259-66.
23. Reed, G., et al., *CALM3 mutation associated with long QT syndrome.* Heart Rhythm, 2014.
24. Gomez-Hurtado, N., et al., *Calmodulin Mutation (CALM1-E141G) Associated with Long QT Syndrome Disrupts Calmodulin Calcium Binding and Impairs L-Type Ca Channel Inactivation.* Heart Rhythm, 2014. 11(11): p. 2135-2136.
25. Boczek, N., et al., *Spectrum and Prevalence of CALM1, CALM2, and CALM3 Mutations in Long QT Syndrome, Catecholaminergic Polymorphic Ventricular Tachycardia, Idiopathic Ventricular Fibrillation, and Sudden Unexplained Death in the Young.* Circulation, 2013. 128: p. A14699.
26. Pipilas, D., Johnson, C N., Webster, G., Schlaepher, J., Fellmann, F., Sekarski, N., Wren, L M., Ogorodnik, K V., Chazin, D M., Chazin, W J., Crotti, L., Bhuiyan, Z A., George Jr, A L, *Novel calmodulin mutations associated with congenital long QT syndrome affect calcium current in human cardiomyocytes.* Heart Rythm, 2016.
27. Yin, G., et al., *Arrhythmogenic calmodulin mutations disrupt intracellular cardiomyocyte $Ca^{2+}$ regulation by distinct mechanisms.* Journal of the American Heart Association, 2014. 3(3).
28. Vincent, G. M., *The long-QT syndrome—bedside to bench to bedside.* N Engl J Med, 2003. 348(19): p. 1837-8.
29. Wilde, A. A. M., et al., *Left Cardiac Sympathetic Denervation for Catecholaminergic Polymorphic Ventricular Tachycardia.* N Engl J Med 2008. 358: p. 2024-2029.
30. Viskin, S., *Long QT syndromes and torsade de pointes.* Lancet, 1999. 354(9190): p. 1625-33.
31. Kathiresan, S. and D. Srivastava, *Genetics of human cardiovascular disease.* Cell, 2012. 148(6): p. 1242-57.
32. Wehrens, X. H., et al., *FKBP12.6 deficiency and defective calcium release channel (ryanodine receptor) function linked to exercise-induced sudden cardiac death.* Cell, 2003. 113(7): p. 829-40.
33. Angrist, M., et al., *Impact of gene patents and licensing practices on access to genetic testing for long QT syndrome.* Genet Med, 2010. 12(4 Suppl): p. S111-54.
34. Kursula, P., *The many structural faces of calmodulin: a multitasking molecular jackknife.* Amino Acids, 2014. 46(10): p. 2295-304.
35. Ben-Johny, M. and D. T. Yue, *Calmodulin regulation (calmodulation) of voltage-gated calcium channels.* J Gen Physiol, 2014. 143(6): p. 679-92.
36. Fallon, J., Halling, D B, Hamilton, S L, Quiocho, F A, *Structure of calmodulin bound to the hydrophonic IQ domain of the cardiac Ca(v)1.2 calcium channel.* Structure, 2005. 13(12): p. 1881-1886.

37. Aykut, A., Atilgan, A R., Atilgan C., *Designing Molecular Dynamics Simulations to Shift Populations of Conformational States of Calmodulin*. PLOS Computational Biology, 2013.
38. Hwang, H.-S., Nitu, F. R., Yang, Y., Walweel, K., Pereira, L., Johnson, C. N., . . . Knollmann, B. C., *Divergent Regulation of Ryr2 Calcium Release Channels by Arrhythmogenic Human Calmodulin Missense Mutants*. Circulation Research, 2014. 114(7): p. 1114-1124.
39. Ben-Johny, M., et al., *Towards a Unified Theory of Calmodulin Regulation (Calmodulation) of Voltage-Gated Calcium and Sodium Channels*. Curr Mol Pharmacol, 2015. 8(2): p. 188-205.
40. Humphrey, W., Dalke, A. and Schulten, K., *VMD—Visual Molecular Dynamics*. Journal of Molecular Graphics, 1996. 14: p. 33-38.
41. Phillips, J., Braun, R., Wang, W., Gumbart, J., Tajkhorshid, E., Cilla, E., Chipot, C., Skeel, R D., Kale, L., Schulten, K., *Scalable molecular dynamics with NAMD*. Journal of Computational Chemistry, 2005. 26: p. 1871-1802.
42. Best, R. B., et al., *Optimization of the additive CHARMM all-atom protein force field targeting improved sampling of the backbone phi, psi and side-chain chi*(1) *and chi*(2) *dihedral angles*. J Chem Theory Comput, 2012. 8(9): p. 3257-3273.
43. Team, R. C., R: *A language and environment for statistical computing*. R Foundation for Statistical Computing, Vienna, Austria https://www.R-project.org/, 2016.
44. Vu, V. Q., *ggbiplot: A ggplot2 based biplot. R package version* 0.55. http://github.com/vqv/ggbiplot, (2011).
45. Deplancke, B., Alpern D., Gardeux, V., *The Genetics of Transcription Factor DNA Binding Variation*. Cell, 2016, 166(3): p. 538-554.
46. Kamanu, F. K., Medvedeva, Y. A., Schaefer, U., Jankovic, B. R., Archer, J. A. C., Bajic, V. B., *Mutations and Binding Sites of Human Transcription Factors*. Front Genet, 2012, 3(100): p. 1-6.
47. Latchman, D. S., *Transcription-Factor Mutations and Disease*. The New England Journal of Medicine, 1996, 334: p. 28-33.
48. Kapeli, K., Martinez, F. J., Yeo, G. W., *Genetic Mutations in RNA-Binding Proteins and Their Roles in ALS*. Hum Genet, 2017, 136(9): p. 1193-1214.
49. Neelamraju Y., Gonzalez-Perez, A., Bhat-Nakshatri, P., Nakshatri, H., Janqa, S. C., *Mutational Landscape of RNA-Binding Proteins in Human Cancers*. RNA Biol, 2018 15(1): p. 115-129.

The invention claimed is:

1. A method comprising:
identifying at least one structure of a wildtype macromolecule;
seeding and executing a plurality of all atom molecular dynamics (MD) simulations using the at least one structure to generate a conformational landscape of the wildtype macromolecule and a plurality of variants of the wildtype macromolecule, wherein generating the conformational landscape comprises generating, via the plurality of all atom MD simulations, a plurality of variant structures corresponding to each of the plurality of variants of the wildtype macromolecule;
generating a first dataset by determining, from the conformational landscape, structural features and energetic features of the at least one structure and the plurality of variant structures;
processing the first dataset via a first clustering algorithm to generate a wildtype cluster of the at least one structure and a plurality of variant clusters, wherein each of the plurality of variant clusters defines a respective conformational population comprising a different subset of the plurality of variant structures;
generating a second dataset by quantifying structural and energetic features of the wildtype cluster and the respective conformational population defined by each of the plurality of variant clusters, wherein the structural features and energetic features comprise global structural features, dynamics of structure subdomains, energetic interactions, and overall statistical characteristics of structures;
processing the second dataset via a second clustering algorithm to generate a second wildtype cluster and a second plurality of variant clusters;
performing principal component analysis on the second dataset to generate a principal component feature space;
plotting, in the principal component feature space, a wildtype centroid of the second wildtype cluster and a plurality of variant centroids corresponding to each of the second plurality of variant clusters;
calculating, in the principal component feature space, a plurality of Euclidean distances between the wildtype centroid and each of the plurality of variant centroids;
based on the plurality of Euclidean distances, removing a subset of the second plurality of variant clusters that fall within a predetermined clustering threshold of the wildtype centroid, wherein removal of the subset from the principal component feature space generates a plurality of remaining variant centroids;
comparing, in the principal component feature space, each of the plurality of remaining variant centroids to the wildtype centroid; and
based on the comparison, determining a severity ranking of a subset of the plurality of variants of the wildtype macromolecule that are associated with the plurality of remaining variant centroids.

2. The method of claim 1, wherein the plurality of variants of the macromolecule are variant proteins.

3. The method of claim 2, wherein the variant proteins cause a disease.

4. The method of claim 3, wherein variant proteins cause a genetic disease.

5. The method of claim 4, wherein the genetic disease is Long QT Syndrome or Polymorphic Ventricular Tachycardia.

6. The method of claim 2, wherein the method comprises identifying a plurality of variant-specific populations of protein structure conformation based on the wildtype cluster and the variant proteins.

7. The method of claim 6, wherein the first clustering algorithm utilizes root mean square deviation to cluster the first dataset.

8. The method of claim 6, wherein the method comprises quantifying structural and energetic features of individual structures within the respective conformational population defined by each of the plurality of variant clusters.

9. The method of claim 8, wherein:
the second dataset comprises multi-dimensional feature sets; and
processing the second dataset via the second clustering algorithm comprises using unsupervised clustering of the multidimensional feature sets to identify mutant conformational populations which diverge from those found in a subset of the plurality of all atom MD simulation associated with the wildtype macromolecule, thereby identifying divergent variant structures.

10. The method of claim 9, wherein performing principal component analysis on the second dataset comprises performing principal component analysis (PCA) on the multi-dimensional feature sets.

11. The method of claim 10, wherein performing PCA on the multi-dimensional feature sets comprises:
    mapping, in the principal component space, all structures of the multi-dimensional feature sets to a multi-dimensional plot of principal components that define features that characterize and separate different structures in the second dataset; and
    collapsing a distribution of the wildtype centroid and divergent centroids of the plurality of variant centroids into a weighted centroid in the principal component space.

12. The method of claim 11, wherein:
    the wildtype macromolecule is a wildtype protein; and
    the method comprises using the weighted centroid in the principal component space to determine a specific phenotypic disruption and rank a relative functional effect of each of the variant proteins with respect to that of the wildtype protein.

13. The method of claim 12, wherein the ranking of the relative functional effect of each of the variant proteins provides information for distinguishing disease phenotypes caused by at least one of the variant proteins.

14. The method of claim 1, wherein the severity ranking corresponds to functional severity caused by the subset of the plurality of variants of the macromolecule.

15. The method of claim 14, wherein the method further comprises determining one or more functional effects of the subset of the plurality of variants of the macromolecule with respect to binding to a ligand.

16. The method of claim 15, wherein the ligand is an ion, a small molecule, a protein, or a nucleic acid.

17. The method of claim 15, wherein the plurality of variants of the macromolecule are variants of an enzyme and the ligand is a substrate.

18. The method of claim 15, wherein the plurality of variants of the macromolecule are nucleic acids and the ligand is a nucleic acid binding protein.

19. The method of claim 14, wherein the method provides information for designing a drug for treatment of a disease.

20. The method of claim 1, wherein the structural features and energetic features comprise global structural features, dynamics of structure subdomains, energetic interactions, and overall statistical characteristics of structures.

* * * * *